(12) United States Patent
Smith et al.

(10) Patent No.: US 6,357,303 B2
(45) Date of Patent: *Mar. 19, 2002

(54) MECHANICAL TESTING DEVICE

(75) Inventors: Evertt L. Smith, Madison, WI (US); David Jones, Margburg (DE)

(73) Assignee: The National Institute of Biogerontology, Inc., Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/731,430

(22) Filed: Dec. 6, 2000

Related U.S. Application Data (62) Division of application No. 09/110,503, filed on Jul. 6, 1998
(60) Provisional application No. 60/052,587, filed on Jul. 15, 1997.

(51) Int. Cl.[7] .................................................. G01L 1/16
(52) U.S. Cl. .................................................. 73/862.68
(58) Field of Search ........................ 73/763, 777, 790, 73/811, 862.381, 862.68

(56) References Cited

U.S. PATENT DOCUMENTS

| 4,731,044 | A | * | 3/1988 | Mott | .............................. 474/8 |
| 5,383,474 | A | | 1/1995 | Akhter et al. | |
| 5,406,853 | A | | 4/1995 | Lintilhac et al. | |
| 5,463,902 | A | | 11/1995 | Shriver et al. | |
| 5,511,571 | A | * | 4/1996 | Adrezin et al. | ................ 135/66 |
| 5,700,688 | A | | 12/1997 | Lee et al. | |
| 5,767,402 | A | | 6/1998 | Sandlass et al. | |
| 6,171,812 | B1 | * | 1/2001 | Smith et al. | .............. 435/40.52 |
| 6,198,198 | B1 | * | 3/2001 | Fujimura et al. | ...... 310/316.01 |

OTHER PUBLICATIONS

Baron R., Vignery A., Neff L., Silvergalate A., Santa Maria A. (1983). Processing of undecalcified bone specimens for bone histomorphometry. In: ed, Recker R. R., Bone Histomorphometry: Techniques and Interpretation CRC, Boca Raton, FL, 13–35.

Brighton C.T., Sennett B.J., Farmer J. C., Ianotti J. P., Hansen C.A., Williams J. L., Williamson J. The inositol phosphate pathway as a mediator in the proliferative resonse of rat calvarial bone cells to cyclical biaxial mechanical strain. J. Orthop. Res. 10:2850393; 1992.

Carvalho R. S., Scott J. E., Suga D. M., Yen E.H. K. Stimulation of signal transduction pathways in osteoblasts by mechanical strain potentiated by parathyroid hormone. J. Bone Min. Res. 9::99–1011; 1994.

Crenshaw T. D., Thomson B. M., Nobel B. S., Milne J. S. And Loveridge N. Prostaglandin E2 inhibits proliferation of procine progenitor osteoblast cells. J. Bone Min. Res. 8(1):S362, 1993.

(List continued on next page.)

Primary Examiner—Max Noori
(74) Attorney, Agent, or Firm—Lathrop & Clark LLP (57) ABSTRACT

A mechanical testing device has a rigid frame and a piezo translator connected to the frame. A Wheatstone bridge is connected to the translator to produce an electrical signal related to the compression of the translator, wherein a sample positioned between the piezo translator and the frame is subjected to loads by the movement of the translator. A sensor detects the force applied to the sample by the piezo translator, and produces a signal indicative of the force. A computer receives the Wheatstone bridge electrical signal and the signal indicative of the force applied to the sample. The computer controls the advancement of the translator to allow the application of precise amounts of compression to the sample.

3 Claims, 6 Drawing Sheets

OTHER PUBLICATIONS

Currey J. The Mechanical Adaptation of bones. Princeton NJ: Princeton University Press, 1984.

Dalsky G. P., Stocke K. S., Ehsani A. A., Slatopolsky E., Lee W. C. and Birge S. J. Weight–bearing exercise training and lumbar bone mineral content in post menopausal women. Ann. Intern. Med. 108:824–838, 1988.

El Haj A. J., Minter S. L, Rawlinson S. C. F., Suswillo R. and Lanyon L. E. Cellular responses to mechanical loading into vitro. J. Bone Min. Res. 5:923–932, 1990.

Frost H. M. (1983). Bone histomorphometry: analysis of trabecular bone dynamics. In: ed, Recker R. R., bone Histomorphometry: Techniques and Interpretation CRC Press, Boca Raton, FL, 109–142.

Gleeson P. B., Protas E. J., LeBlanc A. D., Schneider V. S. and Evnas H. J. Effects of weight lifting on bone mineral density in premenopausal women. J. Bone, Min. Res. 5:153–157, 1990.

Hock J. M., Centrella M. and Canalis E. Insulin–like growth factor I (alGF–1) has independent effects on bone matrix formation and cell replication. Endocrin. 122:254–260; 1988.

Hsieh H. J., Li N. Q., Frangos J. A. Shear stress increases edothelial platelet–derived growth factor mRNA levels. Am. Physiol J. 260:H642; 1991.

Jones D. B., Nolte H., Scholubbers J. G., Turner E., Veltel D. Biochemical signal transduction of mechanical strain in osteoblast–like cells. Biomaterials. 12:101–110; 1991.

Lanyon L. E. Control of bone architecture by functional load bearing. J. Bone Min. Res. 7:S369–S375, 1992.

Murray D. W. and Rushton N. The effect of strain on bone cell prostaglandin E2 release: a new experimental method. Calcif. Tissue Int. 47:35–39, 1990.

Mundy G. R. Bone resorbing cells. In: Primer on the Metabolic Bone Diseases and Disorders of Mineral Metabolism, Favus M. J. (ed), Kelseyville, California. American Society for Bone and Mineral Research (pp. 18–22) 1990.

Notelovitz M., Martin D., Tesar R., Khan F. Y., Probart C., Fields C. and McKenzie L. Estrogen therapy and variable resistanct weight training increase bone mineral in surgically menopausal women. J. Bone Min. Res. 6:583–590, 1991.

Parfitt A. M., Drezner M. K., Glorieux F. H., Kanis J. A., Malluche H., Meunier P. J., Ott S. M., Ricker R. R. (1987). Bone histomorphometry: standardization of nomenclature, symbols and units. J. Bone Min. Res. 2:595–609.

Parfitt A. M., Mathews C. H. E, Villanueva A. R., Kleerekper M., Frame B., Rao D. S. (1983). Relationships between surface, volume and thickness of iliac trabecular bone in aging and in osteoporosis. J. Clin Inv 72:1396–1409.

Pead M. J., Suswillo R., Skerry, Vedi S., Lanyon L. E. Increased [3H] uridine levels in osteocytes following a single short period of dynamic bone loading in vivo. Calcif. Tissue Int. 43:92–96; 1988.

Parfitt A. M. The physiologic and clinical significance of bone histomorphometric data. In: Bone Histomorphometry: Techniques and interpretation. Recker R. R. (ed) (pp. 143–223) 1983.

Raab D. M., Crenshaw T. D., Kimmel D. B., Smith E. L. A histomorphometric study of cortical bone activity during increased weight–bearing exercise. J. Bone Min. res. 6:741–749, 1991.

Raab–Cullen D. M., Akhter M. P., Dimmel D. B. and Reckr R. R. Periostearl bone formation stimulated by externally inducted bending strains. J. Bone Min. Res. 9:1143–1152; 1994.

Raab–Cullen D. M., Thiede M. A., Petersen D. N., Kimmel D. B., Recker R. R. Mechanical loading stimulates rapid changes in periosteal gene expression. Calcif. Tissue Int. 5:473–478; 1994.

Rawlinson S. C. F., Mohan S., Baylink D. J., Lanyon L. E. Exogenous prostacyclin, but not prostaglandin E2, produces similar responses in both G6PD activity and RNA production as mechanical loading and increases IGF–II release in adult cancellous bone in culture. Calcif. Tissue Int. 53:324–329; 1993.

Rubin C. T. and Lanyon L. E. Regulation of bone mass by mechanical strain magnitude. Calcif. . Tissue Int. 37:411–417, 1985.

Smith E. L. and Gilligan C. Dose–response relationship between physical loading and mechanical competence of bone. Bone 18:45S–50S; 1996.

Smith E. L., Gilligan C., McAdam M., Ensign C. P. and Smith P. E. Deterring bone loss by exercise intervention in premenopausal and postmenopausal women. Calcif. Tissue Int. 44:312–321, 1989.

Tommerup L. J., Raab D. M., Crenshaw T. D. and Smith E. L. Does weight–bearing exercise affect non–weight bearing bone? J. Bone Min. Res. 8(9): 1053–1058, 1993.

Turner C. H., Woltman T. A. and Belongia D. A. Structural changes in rat bone subjected to long–term in vivo mechanical loading. Bone 13:417–422, 1992.

Turner C. H. Mechanical loading thresholds for lamellar and woven bone formation. J. Bone Min. Res. 9:87–97, 1994.

"Micro Bionix 250 Testing System. . . " MTS Systems Corporation, Nov. 12, 1998. http://www.mts.com/pr/pr981112.htm.

"The 858 Mini Bionix II Test System. . . " MTS Systems Corporation. http://www.mts.com/menusystem.asp?DataSource=0&NodeID=186.

\* cited by examiner

MECHANICAL TESTING DEVICE

CROSS REFERENCES TO RELATED APPLICATIONS

This application is a divisional of U.S. application Ser. No. 09/110,503, filed Jul. 6, 1998, which claimed priority based on U.S. provisional application No. 60/052,587, filed Jul. 15, 1997, the disclosures of both said applications being incorporated by reference herein.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The present invention is in the field of biotechnology and specifically relates to the study of the physiological and physiochemical processes which govern and underlie the formation, growth and resorption of human and animal bone. In particular the invention provides novel means for the study of responses of the mammalian musculoskeletal system to stress and potentially may lead to the discovery of novel substances produced by bone during these responses. The instant system may lead to a better understanding of diseases such as osteoporosis and the perfusion chamber means provides means for the study of the effects of drugs and other substances added to the perfused medium.

It has been known for over 150 years that bone responds to mechanical loading. Although the effects of exercise and mechanical loading on the musculoskeletal systems have been well documented, the actual mechanisms by which mechanical loading acts at the cellular level in the maintenance of skeletal integrity are not completely understood. Although greater attention is being given to exercise and nutrition as a means of preventing and/or treating osteoporosis, the regulatory mechanisms that control skeletal response to mechanical loading, growth factors and nutrition are not yet delineated.

There is speculation about the biophysical structure and properties of the sensory and biochemical and molecular biological mechanism of mechano-transduction. When controlled loads of a given magnitude and frequency are applied, in vivo, either in an isolated wing preparation or a rat tibia, bone mineral density is known to increase to an extent which is approximately proportional to the load applied. However, according to the prior art, it is not possible to assess quantitatively the bone-specific regulatory control product and their mechanisms nor to monitor the bone production of local growth factors and cytokines, in these in vivo preparations.

Whilst cell culture preparations do permit an investigator to quantify second messengers, cytokines and local growth factors, they do not permit one to monitor the responses of bone cells to mechanical deformation of the bone matrix which are so important in maintaining and/or remodeling of the skeletal system.

Although growth factors have been shown to enhance the development of new bone, clearly and without the presence of mechanical loading, under these circumstances, the new matrix is not formed along lines of strain and it is that feature, in life, which induces maximum integrity of the new bone so formed. The present authors have been associated with previous work in which the viability of osteoblasts from 2 to 4 week old pigs was successfully maintained, in culture, for 68 days. Careful consideration of these findings led to the hypothesis that, in a suitable novel system, which would permit continuous perfusion and mechanical loading of suitable explanted samples of trabecular bone from mature pigs, viability might be maintained for 10 to 12 days or longer. If this were to be achieved, such a time frame would permit measurements of the rate of bone formation and resorption of the trabecular bone, not available using the systems, apparatus and methods of the prior art. Further, such a novel system would be applicable to the study of human bone.

Up to now, prior art apparatus and systems for investigating bone have either comprised cell culture apparatus of a variety of well-known types or mechanical means for applying three point and four point bending forces to a biological test subject. An example of the three point type is disclosed in U.S. Pat. No. 5,406,853 to Lintilhac and Vesecky and an example of the four point type is disclosed in U.S. Pat. No. 5,383,474 to Recker and Akhter.

The present authors are not aware of any prior art system or apparatus which provides means for simultaneous, contemporaneous and continuous study of axially loaded viable mammalian bone undergoing concurrent continuous perfusion and the effluent medium therefrom.

References

1. Baron R., Vignery A., Neff L., Silverglate A., Santa Maria A. (1983). Processing of undecalcified bone specimens for bone histomorphometry. In: ed, Recker R. R., Bone Histomorphometry: Techniques and Interpretation CRC, Boca Raton, Fla., 13–35.
2. Brighton C. T., Sennett B. J., Farmer J. C., Ianotti J. P., Hansen C. A., Williams J. L., Williamson J. The inositol phosphate pathway as a mediator in the proliferative response of rat calvarial bone cells to cyclical biaxial mechanical strain. J. Orthop. Res. 10:385–393; 1992.
3. Carvalho R. S., Scott J. E., Suga D. M., Yen E. H. K. Stimulation of signal transduction pathways in osteoblasts by mechanical strain potentiated by parathyroid hormone. J. Bone Min. Res. 9::999–1011; 1994.
4. Crenshaw T. D., Thomson B. M., Noble B. S., Milne J. S. and Loveridge N. Prostaglandin E2 inhibits proliferation of porcine progenitor osteoblast cells. J. Bone Min. Res. 8(1):S362, 1993.
5. Currey J. The Mechanical Adaptation of bones. Princeton N.J.: Princeton University Press, 1984.
6. Dalsky G. P., Stocke K. S., Ehsani A. A., Slatopolsky E., Lee W. C. and Birge S. J. Weight-bearing exercise training and lumbar bone mineral content in post menopausal women. Ann. Intern. Med. 108:824–828, 1988.
7. El Haj A. J., Minter S. L., Rawlinson S. C. F., Suswillo R. and Lanyon L. E. Cellular responses to mechanical loading into vitro. J. Bone Min. Res. 5:923–932, 1990.
8. Frost H. M. (1983). Bone histomorphometry: analysis of trabecular bone dynamics. In: ed, Recker R. R. Bone Histomorphometry: Techniques and Interpretation CRC Press, Boca Raton, Fla., 109–142.
9. Gleeson P. B., Protas E. J., Le Blanc A. D., Schneider V. S. and Evans H. J. Effects of weight lifting on bone mineral density in premenopausal women. J. Bone, Min. Res. 5:153–157, 1990.
10. Hock J. M., Centrella M. and Canalis E. Insulin-like growth factor I (aIGF-1) has independent effects on bone matrix formation and cell replication. Endocrin. 122:254–260; 1988.
11. Hsieh H-J., Li N. Q., Frangos J. A. Shear stress increases endothelial platelet-derived growth factor mRNA levels. Am. Physiol J. 260:H642–646; 1991.

12. Jones D. B., Nolte H., Scholubbers J. G., Turner E., Veltel D. Biochemical signal transduction of mechanical strain in osteoblast-like cells. Biomaterials. 12:101–110; 1991.
13. Lanyon L. E. Control of bone architecture by functional load bearing. J. Bone Min. Res. 7:S369–S375, 1992.
14. Murray D. W. and Rushton N. The effect of strain on bone cell prostaglandin E2 release: a new experimental method. Calcif. Tissue Int. 47:35–39, 1990.
15. Mundy G. R. Bone resorbing cells. In: Primer on the Metabolic Bone Diseases and Disorders of Mineral Metabolism. Favus M. J. (ed), Kelseyville, Calif. American Society for Bone and Mineral Research (PP.18–22) 1990.
16. Notelovitz M., Martin D., Tesar R., Khan F. Y., Probart C., Fields C. and McKenzie L. Estrogen therapy and variable resistance weight training increase bone mineral in surgically menopausal women. J. Bone Min. Res. 6:583–590, 1991.
17. Parfitt A. M., Drezner M. K., Glorieux F. H., Kanis J. A., Malluche H., Meunier P. J., Ott S. M., Recker R. R. (1987). Bone histomorphometry: standardization of nomenclature, symbols and units. J. Bone Min. Res. 2:595–609.
18. Parfitt A. M., Mathews C. H. E., Villanueva A. R., Kleerekoper M., Frame B., Rao D. S. (1983). Relationships between surface, volume and thickness of iliac trabecular bone in aging and in osteoporosis. J Clin Inv 72:1396–1409.
19. Pead M. J., Suswillo R., Skerry, Vedi S., Lanyon L. E. Increased [3H]uridine levels in osteocytes following a single short period of dynamic bone loading in vivo. Calcif. Tissue Int. 43:92–96; 1988.
20. Parfitt A. M. The physiologic and clinical significance of bone histomorphometric data. In: Bone Histomorphometry: Techniques and interpretation. Recker R. R. (ed) (PP.143–223) 1983.
21. Raab D. M., Crenshaw T. D., Kimmel D. B., Smith E. L. A histomorphometric study of cortical bone activity during increased weight-bearing exercise. J. Bone Min. Res. 6:741–749, 1991.
22. Raab-Cullen D. M., Akhter M. P., Dimmel D. B. and Recker R. R. Periosteal bone formation stimulated by externally induced bending strains. J. Bone Min. Res. 9:1143–1152; 1994.
23. Raab-Cullen D. M., Thiede M. A., Petersen D. N., Kimmel D. B., Recker R. R. Mechanical loading stimulates rapid changes in periosteal gene expression. Calcif. Tissue Int. 5:473–478; 1994.
24. Rawlinson S. C. F., Mohan S., Baylink D. J., Lanyon L. E. Exogenous prostacyclin, but not prostaglandin E2, produces similar responses in both G6PD activity and RNA production as mechanical loading and increases IGF-II release in adult cancellous bone in culture. Calcif. Tissue Int. 53:324–329; 1993.
25. Rubin C. T. and Lanyon L. E. Regulation of bone mass by mechanical strain magnitude. Calcif. Tissue Int. 37:411–417, 1985.
26. Smith E. L. and Gilligan C. Dose-response relationship between physical loading and mechanical competence of bone. Bone 18:45S-50S; 1996.
27. Smith E. L., Gilligan C., McAdam M., Ensign C. P. and Smith P. E. Deterring bone loss by exercise intervention in premenopausal and postmenopausal women. Calcif. Tissue Int. 44:312–321, 1989.
28. Tommerup L. J., Raab D. M., Crenshaw T. D. and Smith E. L. Does weight-bearing exercise affect non-weight-bearing bone? J. Bone Min. Res. 8(9): 1053–1058, 1993.
29. Turner C. H., Woltman T. A. and Belongia D. A. Structural changes in rat bone subjected to long-term in vivo mechanical loading. Bone 13:417–422, 1992.
30. Turner C. H. Mechanical loading thresholds for lamellar and woven bone formation. J. Bone Min. Res. 9:87–97, 1994.

OUTLINE OF THE PRESENT INVENTION

In the instant system, apparatus means is provided for the perfusion and axial mechanical loading of an explanted sample of mammalian trabecular bone which has been prepared in an appropriate manner. During use, a prepared trabecular bone biopsy core is placed within the apparatus and is then loaded mechanically to induce tension and/or compression to the bone matrix. The bone explant perfusion and loading apparatus of the instant system is provided with means for maintaining an environment with stable oxygen, carbon dioxide, nutrients and systemic hormones.

Prepared bone biopsies are in the form of trabecular bone cores, 10–12 mm in diameter and 3 to 5 mm thick. These are surgically extracted, under sterile conditions, from suitable long bones of the subject. This procedure is carried out with care and precision, using suitable cutting means and cooling means, to ensure that the resultant bone disk samples are not subjected to temperature rises during cutting and that extreme dimensional accuracy and disk flatness are achieved.

Cutting means are in the form of a surgical hand saw used to cut gross samples, a diamond tipped keyhole saw to remove bone cores from the gross samples and an ultra high precision band saw with a diamond tipped bladed, operated in conjunction with jig means, to cut bone disk. Trabecular bone sample disks produced are flat (±100 nm) and have parallel end surfaces (±2–5 cm). Cooling means comprise suitable phosphate buffered saline (PBS) at 6° C. which is used to flood the work piece during cutting. Each trabecular bone sample disk, so prepared, is intended to supply about 3,500,000–11,000,000 cells (based on an estimate of 10,000–20,000 cells per cubic mm of bone (Mundy 1990; Parfitt 1983). Extracted bone disk samples are perfused and maintained with suitable circulating medium, Hepes and fetal calf serum.

The apparatus of the instant invention provides means for concurrent mechanical loading of the prepared bone explant sample disk, located within a novel perfusion chamber, in a controlled manner. The maximum compressive strain applied to each sample is 0.5% (5,000 $\mu E$) generally at 1 Hz, with the capability of using steeper rise times, if desired. These figures translate to a maximum compression, in each sample, of 20 $\mu m$, at a rate of 50,000 $\mu E$ sec$^{-}$. Further, the apparatus applies to the bone sample disks, controlled deformations of 200 nm. The apparatus applies forces of up to 800N, at frequencies in the physiological range, of up to 15 Hz and maximum strain rates of between 10,000 $\mu E$ sec$^{-1}$ and 50,000 $\mu E$ sec$^{-1}$. These data are appropriate to samples of spongy mammalian bone in which Young's modulus varies between 400 MPa and 1200 Mpa.

The apparatus of the instant system also provides an environment in which many factors can be investigated. Because whole tissue is used, bone cells can be studied in a near-natural environment of bone matrix and bone marrow. The apparatus provides means for the user to monitor cellular response but additionally and in a novel manner, to monitor the architecture, strain characteristics and strength of the bone disk and changes therein.

The bone explant perfusion and mechanical loading apparatus of the present invention preserves the hard matrix of the bone sample and permits the collection of second messengers and growth factors in the perfusion medium. The instant system thus has many of the advantages of cell culture, whilst retaining the bone matrix encountered in vivo.

Means provided within the instant system permit recording of changes in the explanted trabecular bone core sample and further permit the calculation of strain, load and Young's modulus for each such sample. Thus, the instant system permits not only the monitoring of second messengers, cytokines and growth factors but further permits study of how these factors, in conjunction with mechanical loading, will maximize skeletal response to varied stimuli both alone and in combination.

In the instant system there are provided perfusion loading apparatus means, power means, control means, computer hardware means, software means and sampling and analysis methods.

The perfusion loading apparatus comprises frame means, adjustable biasing pre-loading means, translator loading means, force sensor means and perfusion chamber means. Most components are substantially cylindrical and are accurately machined in corrosion resistant metal, conveniently stainless steel.

Frame mounting means are in the form of a relatively massive cylindrical frame housing, comprising a base, a lower frame section, an upper frame section and a cap, each adapted to fit together. These components are secured together with a series, conveniently of 6, partially male-threaded hardened steel bolts which pass through the frame components and are each tightened down with a female-threaded nut. The frame is about 150 mm high and about 80 mm in diameter. The lower part of the frame is substantially solid and has an axial cylindrical hole to accept a ceramic stacked piezo translator which is secured in place by virtue of a close fit in the lower frame and also by screw means through the base.

The top part of the frame provides mounting means for adjustable biasing pre-loading means provided by adjustable screw means located axially in and through and the frame cap and secured thereto by threaded means. Within the adjustable biasing pre-loading means there is provided locating and bearing means for force sensor means in the form of an annular quartz crystal force sensor in a precision welded housing.

The perfusion chamber assembly is located axially and centrally in the upper section of the frame and comprises a stainless steel bottom bearing cap which provides mounting means for a perfusion chamber body made in durable biologically inert, non-leaching plastics, preferably polycarbonate. A piston, conveniently made in stainless steel, is provided with sealing means in the form of an 'O' ring, made from resilient and biologically inert material, preferably neoprene, engages with the upper part of the perfusion chamber body and under the influence of the pre-loading and loading entities, bears down upon a cylindrical explanted trabecular bone sample placed therein. Fluid pathways formed in the perfusion chamber body are disposed so as to ensure that perfusing fluid reaches all parts of the bone sample. Spigots provide connecting means for suitable tube means for delivering perfusing fluid to the assembled perfusion chamber and for collecting effluent from it.

The upper and lower components of the perfusion chamber are provided with locating and compression centering means and the assembly is located axially above and upon the translator loading means and directly beneath and in contact with the adjustable pre-load means which drive through push rod and ball bearing coupling means.

The piezo translator is provided, via cable connecting means, with a suitable control interface having a microprocessor controlled digital to analogue converter, low voltage driver, controller and power supply, a high voltage amplifier and display unit, all having performance and operating characteristics appropriate to the functional applications of the instant system.

The force sensor is provided, via cable connecting means, with a suitable force amplifier having an appropriate power supply and display unit, all having performance and operating characteristics appropriate to the functional applications of the instant system.

It will now be apparent that frame means, in co-operation with adjustable biasing pre-load means having force sensor means, translator loading means and perfusion chamber means, as hereinbefore described, constitute perfusion means and instrumented axial press means for the perfusion and mechanical loading of an explanted human or animal bone sample.

An explanted trabecular bone sample, prepared as hereinbefore described, is placed within the perfusion chamber, which is then assembled to the frame and loading apparatus. With connections established, power on, and perfusing fluid flowing, the adjustable biasing pre-loading sub-system is adjusted to remove lost motion from and to apply a biasing force to the load train. The biasing force is applied using a large load adjustment knob situated above the frame which drives the adjustable biasing pre-loading means via fine-threaded screw means. A suitable biasing pre-load may also be established using electro-mechanical means via regulator loop means provided in the translator controller. Establishment of a biasing force allows system integrity to be checked. The desired working load or linear translation for the experiment in hand may then be effected using the translator and translator controller.

Serial samples of effluent may be collected and assayed for one or more selected factors. Voltage outputs from the translator and charge output from the force sensor are processed and displayed visually. These are used for input to a suitable standard personal computer employing a standard operating system and running a bespoke software program for manipulating data. The program provides software means which produce outputs, via a standard interface, to the system for set-up, configuration, calibration and control of hardware as well as for calculation of relaxation and Young's modulus. Numerical and graphical results may be output to a suitable monitor and printing device connected to the computer.

The instant system allows assessment of bone cellular response to specific stimuli, under controlled conditions. An understanding of these mechanisms will allow their manipulation which may possibly lead to the alleviation or control of osteoporosis and other deleterious skeletal changes. The instant system advances the state art in permitting investigators to study physiological responses of bone tissue under specified conditions. The instant system also advances the state of the art in permitting study of human bone biopsies in a controlled environment. It provides means for identifying morphologic changes occurring in different bone diseases and potentially, for the determination of the physiologic and genetic determinants in such diseases.

It is thus a first and most important object of the present invention to provide a novel system for continuous perfusion in conjunction with mechanical loading and for collecting and monitoring second messengers, cytokines and growth factors produced by a viable explanted bone sample in order to study skeletal response to varied stimuli both alone and in combination.

It is a second important object of the present invention to provide novel means within the instant system for recording changes in thickness of an explanted bone sample during mechanical loading and further for the calculation of strain, load and Young's modulus for each such sample.

It is a third important object of the present invention to provide novel apparatus means for concurrent perfusion and axial mechanical loading of an explanted sample of mammalian bone, prepared in an appropriate manner, for an extended period during which the bone is to be kept viable.

It is a fourth object of the present invention to provide suitable control and recording means for novel apparatus means for concurrent perfusion and axial mechanical loading of an explanted sample of mammalian bone.

The instant system will now be described in more detail in conjunction with the following drawings.

DESCRIPTION OF THE DRAWINGS

In order that the present invention may be more readily understood, reference will now be made to the following drawings in which.

DESCRIPTION OF THE PREFERRED EMBODIMENTS

With general reference to FIGS. 1–7, there is described a preferred embodiment of a novel, combined perfusion and mechanical loading system for explanted bone, generally designated by the numeral 10.

Referring to the FIGS. 1–7, there are shown the principal assemblies of a perfusion and mechanical loading system 10, comprising metal frame housing means 100, adjustable biasing pre-loading means 400, translator loading means 600, force sensor means 700, perfusion chamber means 800, and electronic control means 900.

Figure 1:
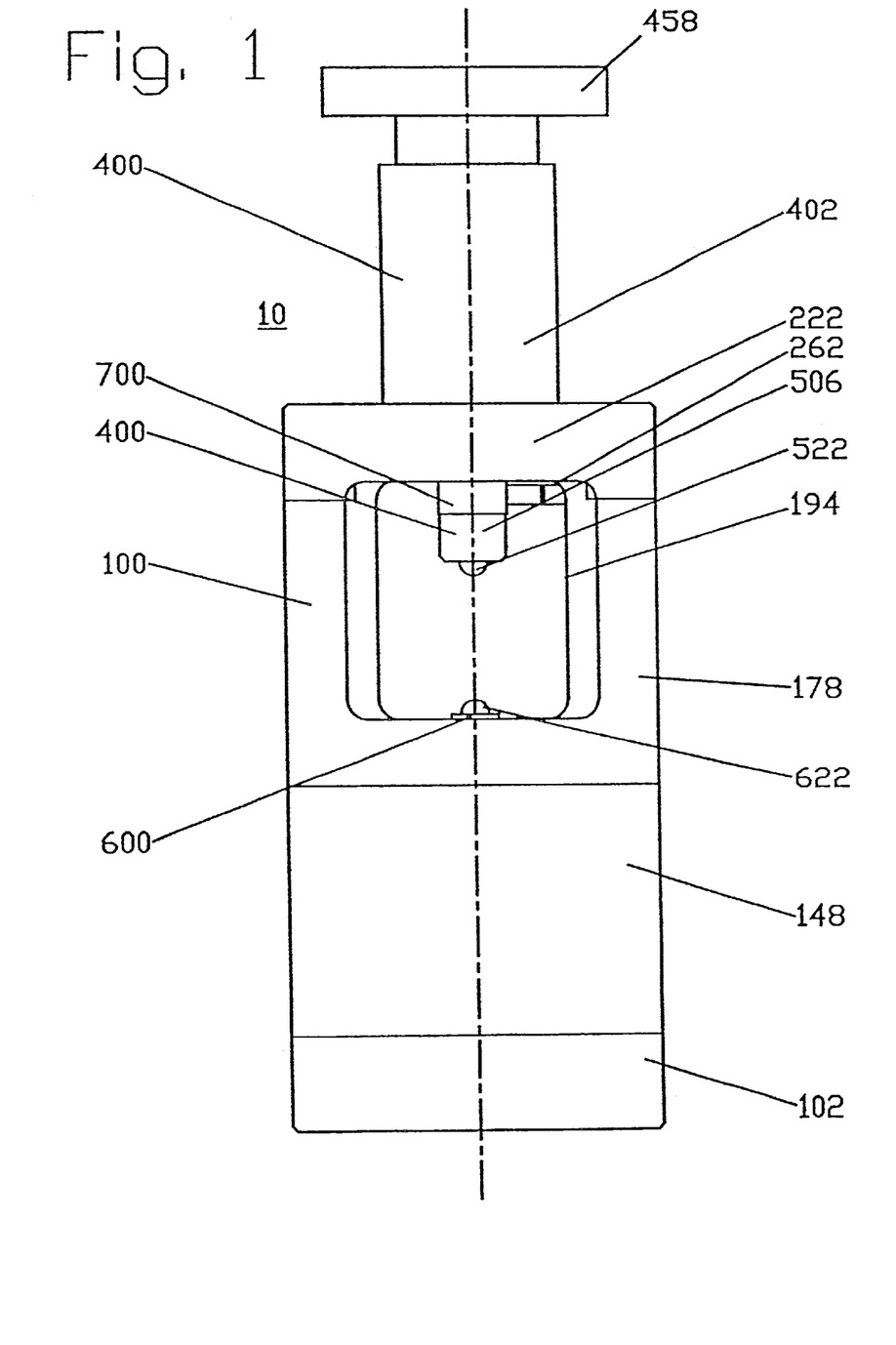
FIG. 1, is a diagrammatic front view of the assembled mechanical and electro-mechanical components of a bone explant perfusion and mechanical loading system, according to the present invention.
Figure 2:
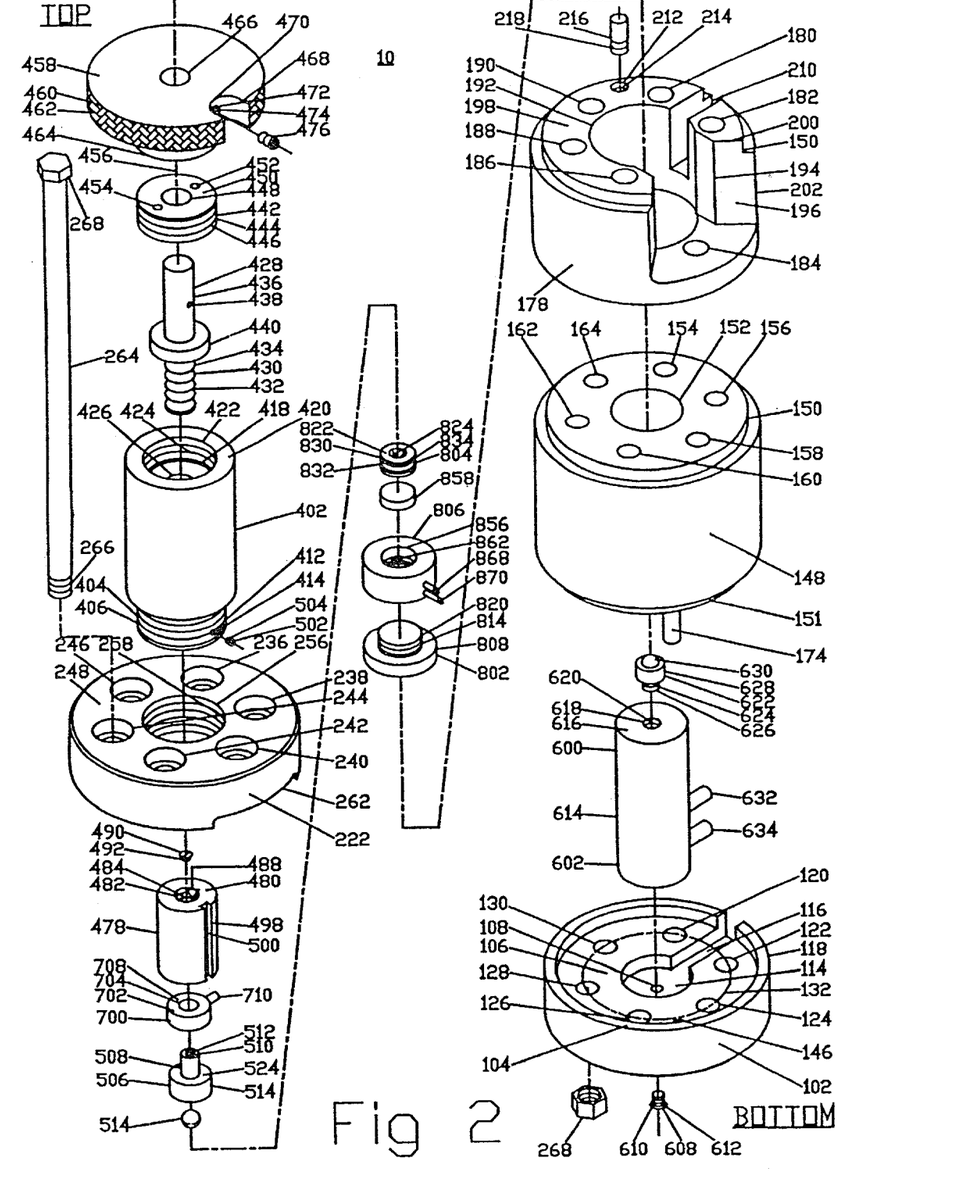
FIG. 2, is a diagrammatic exploded upper perspective axial view of the mechanical and electro-mechanical components of FIG. 1.
Figure 3:
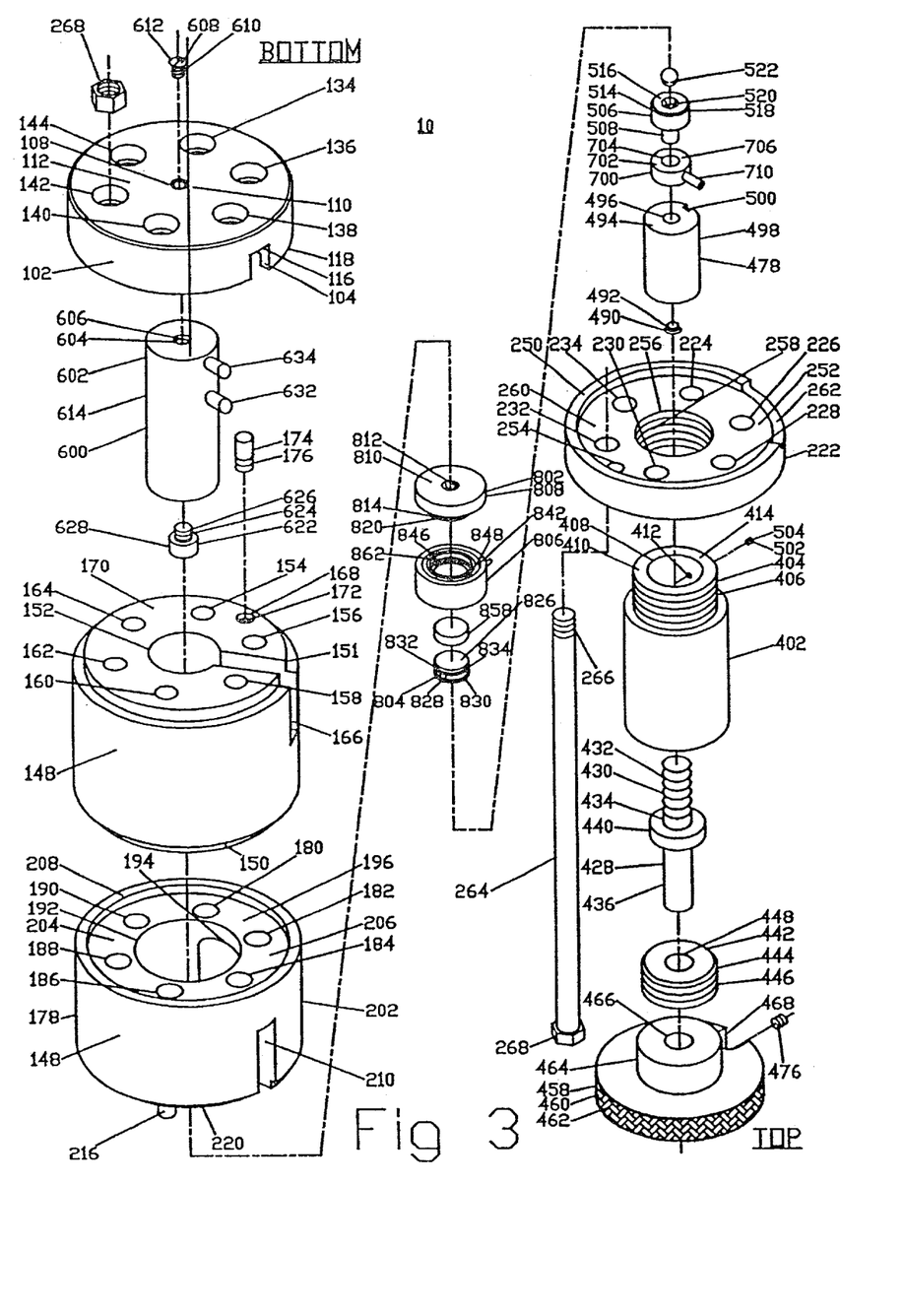
FIG. 3, is a diagrammatic exploded inverted perspective axial view of the mechanical and electro-mechanical components of FIG. 1.

As may best be seen with reference to FIGS. 2 and 3, metal frame housing means 100, are in the form of a substantially cylindrical and relatively massive metal frame, preferably made from solid stainless steel and comprising several accurately machined parts. In this embodiment, a frame base 102, is substantially circular, conveniently having a diameter and general thickness of 78 mm and 15 mm, respectively. Additionally, frame base 102, has a substantially circumferential rim 104, conveniently 4 mm wide and extending somewhat less than 5 mm above general upper surface 106, of 102. A central circular through hole 108, in frame base 102, conveniently 4 mm in radius, has a countersunk recess 110, on the under surface 112, of 102. A central circular recess 114, provided in upper surface 106, of frame base 102, is co-axial with central hole 108. Circular recess 114, has a radius and depth conveniently of 12.5 mm and 5 mm, respectively. A parallel sided recess 116, conveniently 9 mm wide, extends from recess 114, to the edge 118, of frame base 102, interrupting rim 104, thereof. The depth of parallel sided recess 116, is substantially similar to that of circular recess 114. A plurality of clearance fixing holes, 120–130, have centers disposed at equal angles around a pitch circle 132, shown as a center line, conveniently of radius 25 mm and concentric with 108. Fixing holes, 120–130, are each adapted by the provision of a counter bore 134–144, on under surface 112, of frame base 102. Frame base 102, is provided with a counter bore 146, disposed in its upper surface 106, having a diameter and depth, conveniently, of 6 mm and 7 mm, respectively. Counter bore 146, is centered on a line bisecting the angle between holes 124; 126, substantially midway between pitch circle 132, and rim 104 of 102.

A lower frame section 148, is substantially of similar radius to frame base 102. Lower frame section 148, conveniently has a height of 61 mm and is provided with substantially circumferential right angled rebates of 5 mm, top and bottom, indicated at 150 and 151, respectively. A central circular through-hole 152 and a series of fixing holes 154–164, are provided which have substantially similar diameters to and relative spatial dispositions corresponding with 114 and 120–130, respectively, of frame base 102. Similarly, a parallel sided recess 166 and a counter bore 168, are provided in the underside 170, of lower frame section 148, having dimensions and positions which correspond with 116 and 146 of 102. Counter bore 168, is adapted by the provision of female thread means 172. A locating stud 174, adapted by the provision of partial male thread means 176, threadedly engages with the female thread means 174, of counter bore 168. Lower rebate 151 and locating stud 174, of lower frame section 148, together with rim 104 and counter bore 146, of frame base 102, constitute adaptations for mutual location and secure positioning means.

An upper frame section 178, has a height, conveniently, of 65 mm and is of similar radius to 102 and 148. Additionally and also similarly, upper frame section 178, is provided with a series of fixing holes 180–190, which have substantially similar diameters to and relative spatial dispositions corresponding to 154–164, of lower frame section 148 and 120–130, of frame base 102. A central circular hole 192, has a diameter, conveniently, of 37 mm. Observation means are in the form of a parallel sided fenestration slot 194, conveniently 30 mm wide, extending from 192, through wall 196, of upper frame section 178, from its upper surface 198, to a depth, conveniently, of 50 mm. Fenestration slot 194, is symmetrically disposed about fixing hole 184 and has a deep chamfer 200, extending out to a width, conveniently, of 53 mm at the outer surface 202, of 178. Lower surface 204, of upper frame section 178, is adapted by the provision of a machined recess 206, to form a rim 208, so dimensioned as to constitute engagement location means for positioning upon upper rebate 150, of lower frame section 148. A further parallel sided slot 210, has substantially the same width and is in a corresponding position to recesses 116; 166, of frame base 102 and lower frame section 148, respectively. Slot 210, extends from central hole 192, through wall 196, to outer surface 202 and extends to a depth, conveniently of 25 mm, from upper surface 198, of the 178. A counter bore 212, in upper surface 198, of 178, is provided with female thread means 214. A locator stud 216, is provided with partial male thread means 218, for threaded engagement with female thread means 214, of counter bore 212. Counter bore 212 and locator stud 216, are of substantially similar dimensions and are similarly spatially disposed to 168 and 174, of lower frame section 148. Upper surface 198, of upper frame section 178, has a circumferential rebate 220, substantially similar to 150, of lower frame section 148.

A frame cap 222, has a similar diameter and thickness to frame base 102. Frame cap 222, is provided with fixing holes 224–234, substantially similar in diameter and disposition to, those of frame base 102. Fixing holes, 224–234, are each adapted by the provision of a counter bore 236–246, in upper surface 248, of 222, substantially similar to 134–144, in 112, of frame base 102. Additionally, frame cap 222, has a rim 250, disposed circumferentially about its lower surface 252, substantially similar to rim 104, of frame base 102. A counter bore 254, is adapted and positioned to receive locator stud 216, of upper frame section 178. Rim 250 and counter bore 254, of frame cap 222, together with rebate 220 and locating stud 216, of upper frame section 178, constitute adaptations for mutual location and secure positioning means. A central circular through-hole 256, adapted by the provision of female thread means 258, has a diameter, conveniently, of 30 mm. A central circular recess 260, in upper surface 248, of frame cap 222, is conveniently 40 mm in diameter with a filleted circumference to its full depth, conveniently of 4 mm. Rim 250, is partially interrupted by a shallow cut out 262, so sized and positioned as to correspond with fenestration slot 194, of 178, in order to extend observation means in metal frame housing 100.

Metal frame housing 100, is assembled by mutually locating and positioning 102, 148, 178 and 222 and securing them together with mutual threaded securing means. These means are in the form of a series of bolts, preferable made in hardened steel and indicated in FIGS. 2 and 3, by example bolt 264. Each bolt has a male-threaded portion, shown on 264, at 266 and extending through corresponding fixing holes 120–130, in 102; 154–164, in 148; 180–190, in 178 and 224–234, in 222. Bolt heads, indicated on 262, by example bolt head 268, locate in corresponding counter bores 236–246 of 222. Bolts, exemplified by bolt 264, are each secured by threaded nut means, in the form of nuts, preferably made of hardened steel and indicated in FIGS. 2 and 3, by example nut 270, such that each is located in corresponding counter bores 236–246 of frame cap 222. Nuts and bolts are evenly tightened using a torque wrench.

Adjustable biasing pre-loading means 400, are in the form of a plurality of substantially cylindrical, accurately machined components preferably made of stainless steel. A housing 402, is conveniently 37 mm in maximum diameter and of 65 mm height. A lower portion 404, is conveniently, 15 mm in height with a diameter of 30 mm and is adapted by the provision of male-threaded means 406, to threadedly engage from above with female thread means 258, of axial circular hole 256, of frame cap 222. An axial lower counter bore 408, having a diameter conveniently of 20 mm, extends upwards from lower surface 410, of 402, conveniently for 30 mm. A through hole 412, conveniently of 4 mm diameter, extends radially through the wall 414, of lower male-threaded portion 404, of 402, into lower counter bore 408, thereof and is adapted by the provision of female-threaded means 416, throughout its length. An axial upper counter bore 418, having substantially the same diameter as 408, extends downwards from upper surface 420, of 402, for 15 mm. A further and larger axial upper counter bore 422, in 420, conveniently having a diameter of 27 mm and a depth of 10 mm, is adapted by the provision of female thread means 424. Upper counter bores 418; 422 and lower counter bore 408, are united by an axial circular through hole 426, conveniently 10 mm in diameter.

An adjusting axial screw 428, conveniently has a length of 60 mm. A lower portion 430, has a diameter conveniently of 10 mm and a length of 25 mm and is adapted by the provision of male thread means 432, conveniently extending 22 mm, the remaining 3 mm, indicated at 434, being plain. An upper plain portion 436, of 428, conveniently has a diameter of 10 mm and a length of 30 mm. Upper, plain portion 436, is provided with radial plain blind hole 438, conveniently situated half way along its length and having a diameter of 4 mm and extending 2 mm in depth. A central plain portion 440, of 428, conveniently has a diameter of 20 mm and a length of 5 mm.

A locking collar 442, is conveniently 27 mm in diameter and 10 mm in depth and is adapted on its outer surface 444, by the provision of male thread means 446, to provide threaded engagement means for receival by the female-threaded means 424, of counter bore 422, of pre-load adjuster housing 402. Locking collar 442, is further adapted by the provision of an axial through hole 448, having a diameter sufficient to provide sliding engagement means for the upper plain portion 436, of pre-load adjusting axial screw 428. Upper surface 450, is provided with a pair of counter bores 452; 454, disposed on the same diameter of 442, either side of and equidistant from axis 456. Counter bores 452; 454, each conveniently have a diameter of 3 mm and extend to a depth of 5 mm and constitute tightening drive means for 442.

A knob 458, conveniently has a diameter of 60 mm and a maximum depth of 20 mm. An upper portion 460, having the full diameter of 458, is conveniently 10 mm deep and has a knurled outer surface 462. A lower portion 464, conveniently has a diameter of 30 mm. Knob 458, is adapted by the provision of an axial through hole 466, having a diameter such as to provide, in co-operation with upper plain portion 436, of load adjusting axial screw 428, easy push-fit means. Knob 458, is further adapted by the provision of a slot 468, conveniently 12 mm wide and extending through the full depth of upper portion 460. Slot 468, has a semicircular inner margin 470, adapted by the provision of a small central hole 472, extending radially into central through hole 466 and is further adapted by the provision of female thread means 474, for the receival of a grub screw 476. Grub screw 476, constitutes engagement locking means between pre-load adjuster knob 458 and pre-load adjusting axial screw 428.

An actuator 478, has external dimensions such that, in cooperation with lower counter bore 408, of pre-load adjuster housing 402, these elements provide fully engage-able sliding push-fit means. The upper surface 480, of 478, is provided with an axial counter bore 482, conveniently having a depth of 23 mm, adapted by the provision of internal female thread means 484, for threaded engagement with lower male-threaded portion 430, of pre-load adjusting axial screw 428. Counter bore 482, is further adapted, at its lower end 486, by the provision of countersink means, the position of which is indicated by arrow 488, in FIG. 2.

Countersink means 488, are for the receival of the head 490, of countersunk screw means 492, conveniently of 4 mm diameter. Lower surface 494, of 478, is provided with a central counter bore 496, conveniently having a diameter of 6 mm and which communicates with counter bore 482. External surface 498, of 478, is provided with vertical, parallel sided groove 500, of such a width and depth as to co-operate, in the assembled condition, with a blunt-nosed grub screw 502, provided with partial male thread means 504, received threadedly in and through hole 412, of housing 402, to provide engagement guiding and rotation restraining means. It will now be understood that with 502, engaged in 500, the latter will be prevented from rotating when knob 458, is used to turn adjusting axial screw 428 and that instead, actuator 478, will be driven up or down, within lower counter bore 408, of housing 402, according to the direction in which knob 458, is turned. It will be further understood that this arrangement together with the threaded engagement between internal female thread means 484, of counter bore 482, of 478, with male-threaded portion 430, of pre-load adjusting axial screw 428, constitute drive means for setting or altering biasing preload.

A push rod 506, has an upper portion 508, so sized as to co-operate, slidingly, both with counter bore 496, in lower surface 494, of actuator 478 and also with force sensor 700, hereinafter described. Upper portion 508, of 506, is adapted by the provision of a central counter bore 510, provided with female thread means 512, for the threaded receival of countersunk screw means 492, which is introduced down upper counter bore 482, actuator 478. Push rod 506 also has a lower portion 514, having a greater diameter than 508. Lower surface 516, of 514, is provided with a small peripheral chamfer 518 and is adapted by the provision of a central, substantially hemispherical, recess 520, providing receival means and compression, locating means for a ball bearing 522, conveniently having a diameter of 6 mm. Ball bearing 522, provides part of means for transmitting and centering loads applied to perfusion chamber means 800, hereinafter described. Upper surface 524, of lower portion 514, provides shoulder bearing means for push rod 506, against force sensor 700.

Translator loading means are in the form of a ceramic stacked piezo translator 600, incorporating multiple strain gauge means and having a maximum translational range of 40 μm. Piezo translator 600, may conveniently be a commercial product such as a P-239.30, incorporating an optional module P-177.10, having four strain gauges (Physik Instrumente GmbH, Germany). Piezo translator 600, is substantially cylindrical in form and has a base portion 602, for which circular recess 114, in upper surface 106, of frame base 102, provides gentle push-fit location means. Translator base portion 602, has a central counter bore 604, which is provided with female thread means 606. Securing means between 600 and 102, comprise countersunk male-threaded screw means 608, having a male-threaded shank 610. Shank 610, passes through central hole 108, in frame base 102 and engages, threadedly, with 606. Countersunk head 612, of 608, is tightened against countersunk recess of 110, of under surface 112, of 102.

Piezo translator 600, has a main body portion 614, having such a diameter that it engages central hole 152, of lower frame section 148, with a sliding push-fit. Main body portion 614, is of such a height that, when fully engaged in assembled metal frame housing 100, its upper surface 616, is substantially level with the bottom of fenestration slot 194, of upper frame section 178. Upper surface 616, of piezo translator 600, is adapted by the provision of an axial counter bore 618, adapted by the provision of female thread means 620, for the threaded receival of a small, substantially cylindrical drive pin 622, having a shank 624, provided with male thread means 626. Drive pin 622, may conveniently be a commercial product such as a P-239.95 (Physik Instrumente GmbH, Germany) described by the manufacturer as a 'top piece'. Body portion 628, of drive pin 622, constitutes boss mounting means for an upper portion 630, which is substantially hemispherical and has a diameter conveniently the same as ball bearing 522, of push rod 506. It is to be understood that 630, provides the remainder of means, hereinbefore described with reference to ball bearing 522, means for transmitting and centering loads applied to perfusion chamber means 800, hereinafter described.

When assembled to metal frame housing 100, connecting means for piezo translator 600, in the form of cable means are so disposed as to lie in parallel sided recesses 116, in upper surface 106, of frame base 102 and 166, in lower surface 170, of 148, providing aperture means constituting access means for cable means to connectors 632 and 634. Piezo translator 600, is provided, via connectors 632 and 634, with electronic control means 900, all having performance and operating characteristics appropriate to the functional applications of the instant system best seen and described hereinafter, with reference to FIG. 6.

Force sensor means are in the form of a quartz crystal force sensor 700, housed in an extremely rigid, precision welded, substantially cylindrical housing 702, having dimensions, conveniently, of outside diameter 14.5 mm, inner diameter 6.5 mm and height 8 mm. Force sensor 700, may conveniently be a commercial product such as a model 9011A device (Kistler AG, Winterthur, Switzerland). Force sensor 700, has an axial through hole 704, for smooth sliding engagement with upper portion 508, of push rod 506. In the assembled condition, lower surface 706, of housing 702, located on 508, bears directly upon upper surface 524, of lower portion 514, which provides shoulder bearing means for push rod 506. Upper surface 708, of 702, is borne upon by lower surface 494, of actuator 478. During use of the instant system, compression of 702, between 506 and 478, provides reactive force means for operation of force sensor 700. Force sensor 700, is provided with connecting means in the form of cable means which, in the assembled condition, pass through parallel sided slot 210, of upper frame section 178. Parallel sided slot 210, constitutes aperture means in 178, for access means for cable means to cable connector 710. Cable connecting means extend from cable connector 710, to electronic control means 900, best seen in and hereinafter described with reference to, FIG. 6.

Figure 4:
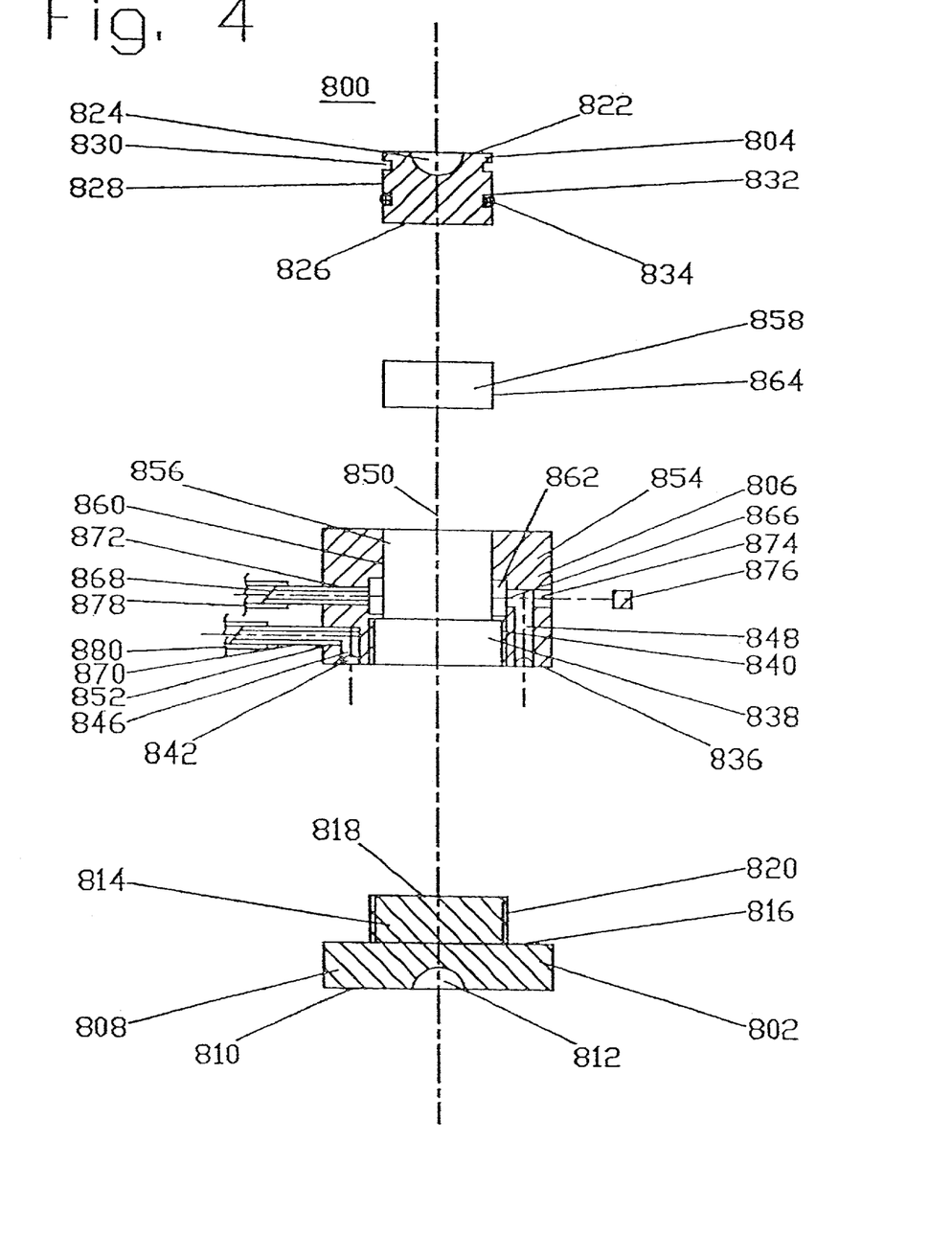
FIG. 4, is a diagrammatic exploded section of the components of the perfusion chamber assembly and a prepared bone sample.
Figure 5:
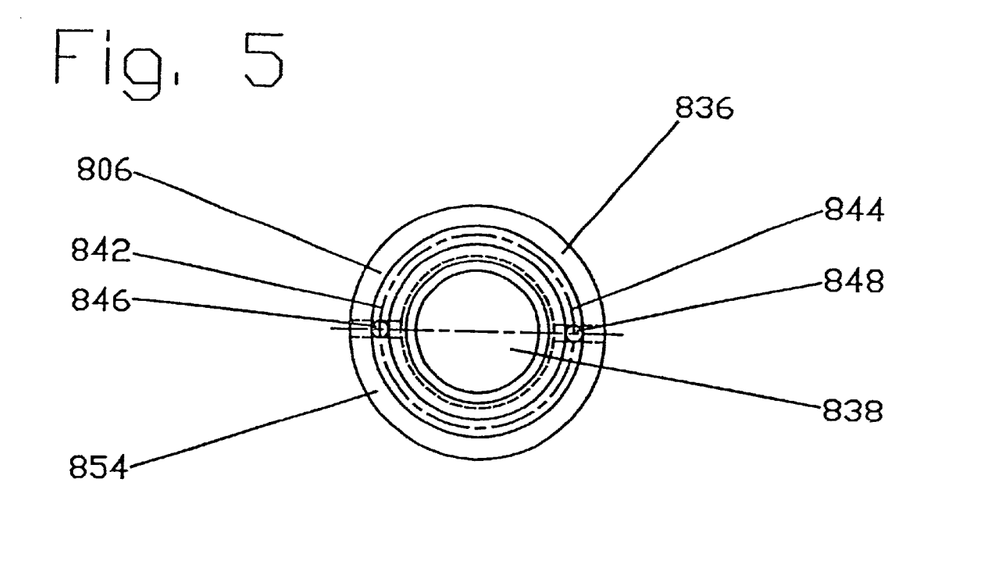
FIG. 5, is an underplan view of the perfusion chamber body of the present invention.
Figure 6:
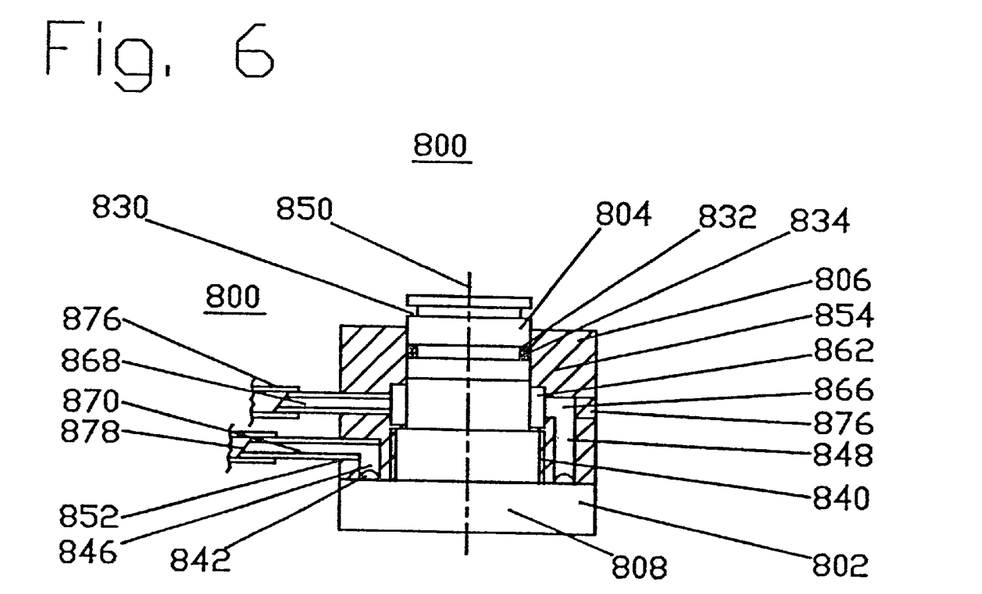
FIG. 6, is a side section of the assembled components of the perfusion chamber assembly with a prepared trabecular bone sample located therein.
Figure 7:
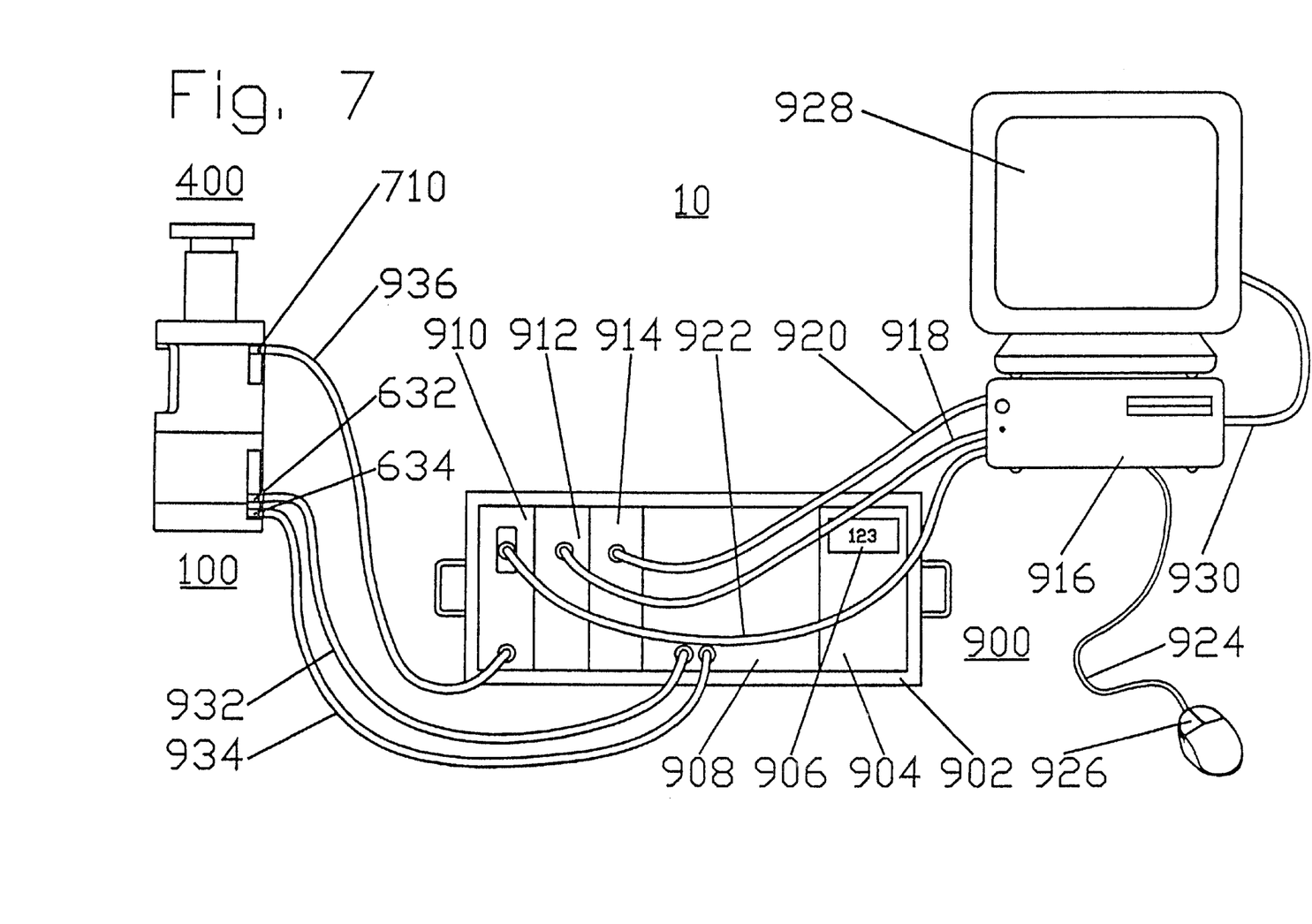
FIG. 7, is a schematic diagram of the instant system particularly illustrating electronic control equipment used in conjunction with the electro-mechanical equipment of the present invention.

Perfusion chamber means 800, best seen in FIGS. 4, 5 and 6, comprise three principal, substantially cylindrical components, a bottom bearing cap 802 and a piston 804, both machined in suitable grades of stainless steel and a perfusion 806, preferably machined from a block of suitable biologically inert, non-leaching plastics, preferably polycarbonate and provided with connection means for perfusion fluid. The choice of plastics is very important since many materials leach substances which are toxic or lethal to cells. Minimally different embodiments may be made in which 806, may be made from suitably biologically inert stainless steels. The preferred embodiment confers the advantage, by virtue of fenestration slot 194, in upper frame section 178, of observability of perfusion during use of system 10.

Bottom bearing cap 802, has a lower portion 808, conveniently having a radius of 25 mm and a depth of 5 mm. Lower surface 810, of 808, is adapted by the provision of an axial, substantially hemispherical, recess 812, providing receival means and compression, locating and centering means for upper hemispherical portion 622, of drive pin 618, of piezo translator 600. Upper portion 814, of 802, conveniently has a diameter of 15 mm and a depth of 5 mm. The upper surfaces 816; 818, of 808 and 814, respectively, are precision ground to flatness and finished by polishing. Upper portion 814, of 802, is provided with male thread means 820. Piston 804, conveniently has a diameter of 12 mm and a height of 8 mm. Upper surface 822, of 804, is adapted by the provision of an axial, substantially hemispherical, recess 824, providing receival means and compression, locating and centering means for ball bearing 522, of push rod 506. Lower surface 826, of piston 804, is precision ground to flatness and finished by polishing. Circumferential wall 828, of 804, is adapted by the provision of an upper and a lower annular groove, indicated at 830 and 832, respectively and mutually disposed apart in a parallel manner to upper and lower surfaces 822 and 826, respectively. Circumferential wall 828, is finished by micro-fine machining and polishing. Lower annular groove 832, constitutes an adaptation for the receival of a sealing means in the form of an 'O' ring 834, made from inert resilient sealing material, preferably neoprene.

Perfusion chamber body 806, conveniently has an outer diameter of 25 mm and a height of 15 mm. Lower surface 836, of 806, is provided with an axial counter bore 838, of such a depth and diameter as to provide, in conjunction with suitable female thread means 840, receival and sealing means for upper portion 814, of bottom bearing cap 802. Lower surface 836, of 806, is precision ground to flatness and is adapted to cooperate with upper surface 816, of lower portion 808, of bottom bearing cap 802 and suitable biologically inert non-leaching adhesive means, to provide additional sealing means between the two components. Lower surface 836, of 806, is further adapted by the provision of a machined annular channel 842, conveniently having a semi-circular cross-section of 2.5 mm diameter and lying on a pitch circle, conveniently 19 mm in diameter and indicated with center line at 844, in FIG. 5. Two small counter bores 846 and 848, having the same diameter as 842, are each centered on the intersection of a diameter of 842 and center line 844, one either side of central axis 850. Small counter bore 846, extends to a depth somewhat less than that of the main lower axial counter bore 838. A radial hole 852, having the same diameter as counter bore 846, extends through wall 854, of 806, so as to meet 846, at right angles, forming substantially continuous lumen means. An upper axial counter bore 856, is so sized and adapted that it may receive an explanted trabecular bone sample 858, prepared as hereinafter described, as a sliding fit and also may engage the greater part of piston 804, as an easy push fit. Lower annular groove 832, of piston 804 and 'O' ring 834, located therein, are particularly included in the engagement between piston 804 and perfusion chamber body 806. Inner surface 860, of upper axial counter bore 856, is adapted by the provision of a parallel sided, annular channel, 862, conveniently 4 mm wide and about 2 mm deep. The position of 862, is such that it substantially surrounds the outer margin or wall 864, of explanted trabecular bone sample 858, when this is inserted in 856, of 806. Second small counter bore 850, extends upwards into 806, to a depth somewhat greater than the depth of main lower axial counter bore 838, such that it terminates at a point substantially level with the mid point of the height of inserted explanted bone sample 858. A diameter hole 866, having the same diameter as small counter bores 846; 848, extends through wall 854, of 806, following the line of radial hole 852, hereinbefore described, intersecting annular channel 862 and also intersecting second small counter bore 848, at right angles, at the limit of its depth, forming further substantially continuous lumen means. Spigots 868 and 870, conveniently fabricated in stainless steel, are adapted to engage, respectively, with radial hole 852 and that portion 872, of diameter hole 866, which lies on the same side of 806, as 852, with a forced, sealing, press-fit. A small cylindrical plug 874, of the same material as 806, is adapted to engage with diameter hole 866, on the opposite side to radial hole 852, with a press-fit in conjunction with suitable biologically inert, non-leaching, adhesive means to provide sealing means between the two components. Plug 874, is of such a length that it extends up to but does not substantially encroach into, second small counter bore 848.

Annular channel 842, of lower surface 836, of perfusion chamber body 806, in cooperation with the upper surface 816, of lower portion 808, of bottom bearing cap 802 and adhesive sealing means; small counter bores 846 and 848, annular groove 862, of upper counter bore 856, radial hole 852 and plugged portion 876, of diameter hole 866, constitute substantially continuous fluid pathway means for perfusing fluid. Spigots 868 and 870, constitute connecting means for suitable tube means in the form of tubes conveniently made of silicone rubber and indicated at 878 and 880, for delivering perfusing fluid to the assembled perfusion chamber and for collecting effluent from it for monitoring and analysis.

It will now be understood that the substantially cylindrical elements of frame means, in co-operation with adjustable biasing pre-loading means having force sensor means, translator loading means having electronic control means and connection means and perfusion chamber means having connecting means for perfusing fluid, as hereinbefore described, constitute instrumented perfusion and axial press means for the perfusion and mechanical loading of an explanted trabecular bone sample.

Performance and Function of Piezo Translator, Force Sensor and Electronic Control Means With particular reference to FIG. 6, as well as continuing reference to FIGS. 2 and 3, electronics control means 900, comprises a rack 902, in which are mounted several major components. A 220V AC power supply 904, also houses a display module 906, which gives readings of high voltage or compression values. A high voltage amplifier 908, provides the high operating voltage (−1000V) to drive piezo translator 600. A controller module 910, includes a compression signal amplifier (not seen) and regulator loop (not seen), to force piezo translator 600, to a required position, within its translational range of 40 μm, corresponding to a given value of high voltage or compression. This range is satisfactory for applications involving explanted bone samples in the instant invention. Controller module 910, may conveniently be a commercial product such as E-255 PZT Interface and Controller (Physik Instrumente GmbH, Germany) which incorporates a digital-analogue converter (DAC). Controller module 910, is linked by cable means (not seen) to low voltage driver and controller 912, which may conveniently be a commercial product such as LVPZ Driver and Controller E-809 (Physik Instrumente GmbH, Germany). Controller module 910, is also linked by cable means (not seen) to a force signal amplifier 914, which is a charge amplifier for amplifying output from force sensor 700.

A personal computer 916, is equipped with a microprocessor of at least 386 rating and is provided, internally, with an additional plug-in card (not seen) which provides a control interface between an analogue-digital converter (ADC) and DAC of 910. Cable 918, connects the additional plug in card of 916, to a compression signal amplifier output provided on low voltage driver and controller 912. Cable 920, connects the additional plug in card of 916, to force signal amplifier 914. Cable 922, connects between a communications port COM-1 (not seen) of 916, to the digital-analogue converter of 910. Cable 924, connects between a communications port COM-2, (not seen) of personal computer 916 and a mouse 926. Personal computer 916, is also provided with a local printer terminal port (not shown) for the connection of a suitable printer (not shown). Personal computer 916, is also equipped with a graphics monitor 928, functioning to EGA, VGA or higher standard to which it is connected by a monitor cable 930. A suitable operating system, such as DOS™ 3.2 or higher or Windows 3.1™ or Windows 95™, is installed on personal computer 916, together with custom software which provides means for coordinating and calibrating the electro-mechanical elements of the system as well as for collecting, collating and displaying data and making calculations thereon and displaying the results thereof.

In FIG. 6, frame means 100 and adjustable biasing preloading means 400, are shown in side view to reveal connecting means for cable means. Cables 932 and 934, connect high voltage amplifier 908, to piezo translator 600, at connectors 632 and 634, respectively. Cable 936, connects force sensor 700, to controller module 910, at connector 710.

Piezo translator 600, incorporates four strain gauges (not seen) attached internally to the ceramic stack and arranged in a full Wheatstone bridge circuit. The multiple strain gauge arrangement may conveniently be in the form of an optional commercial module P-177.10 (Physik Instrumente GmbH, Germany). In conjunction with controller module 910, the bridge arrangement allows a positioning accuracy of 0.2% of the nominal expansion of piezo translator 600, to be achieved.

Force sensor 700, is a quartz crystal force sensor for measuring dynamic and quasi-static forces, having a range of 15 kN, a very high resolution of 0.01N under any pre-load, sensitivity of $\approx -4.3 pC/N$, modulus of 3.6 GPa and very high rigidity of $\approx -1.8 kN/\mu m$. These characteristics are satisfactory for applications involving explanted bone samples in the instant invention.

Experiment 1—Calibration And Validation of Loading Elements Of The System

The instant system was validated and characterized by the following methods:
  a. determination of any errors in the system
  b. identifying deformation accuracy, force application, frequency of loading and calculation of E (Young's modulus) on known materials and determining the physical compliance in the system.

Calibration and validation was accomplished by comparing nondestructive test results of the instant mechanical loading, translator and force sensor elements of the instant system to identical tests run on an MTS (Bionix) servohydraulic test machine. Homogeneous materials, with moduli that span the expected range of cancellous bone, were used (e.g. nylon, aluminum, teflon). These materials had strain gauges applied to the vertical surfaces. Strain was monitored on the same materials in both systems and the results were compared. In addition, a precision extensometer was placed between the platens on the MTS machine to provide specimen deformation, as well as load and thus compute the strain. The current required to achieve similar deformations, strains and loads was recorded. The systems were compared with ramp and sinusoidal wave forms. Hysteresis was noted together with time dependent responses in the materials and test system. The system was the materials and test system. The system was tested quasistatically and at increasing frequencies up to 10 Hz (a functional limit for the MTS system). The system was also tested throughout the range of functional deformation rates available with the piezo crystal translator. Similar specimens were taken to failure and the total material behavior curves of the MTS system and the instant system using the piezo crystal translator, were compared.

Correlation of a very high order was established, validating the prospective deployment of the novel mechanical loading system, in conjunction with the novel perfusion means of the instant invention in explanted trabecular bone samples.

It was determined that the mechanical and electro-mechanical elements of the instant system are capable of applying controlled deformations, accurate to 200 nm, and applying forces of up to 800 N, at frequencies in the physiological range of up to 15 Hz and maximum strain rates of between 10,000 $\mu E$ sec−1 and 50,000 $\mu E$ sec−1. Young's modulus for trabecular bone varies from E=400 MPa to, typically, E=1200 MPa in the adult pig.

Experiment 2—Perfusion

Preparation of Explanted Bone Samples

Features considered when determining the optimal size of the bone sample for the instant system were:

1. The practicality of using cow and pig bone samples in the first instance and the feasibility of using human bone samples, subsequently, having the same dimensions.
2. The volume of bone and means for achieving adequate perfusion through it.
3. The amount of tissue which would be necessary to produce the desired biochemical markers, in quantities sufficient to make the required measurements.

The selection of pig and cow trabecular bone was based on earlier studies by the present authors and other workers. In particular the studies of an associate, Dr. Kit Mui Chiu whose observations were recorded in a doctoral thesis at the University of Wisconsin, presented in 1996 and entitled "The effect of carnitin dehydroepiandrosterone sulfate on young senescent osteoblast-like cells", were important. In these studies pig osteoblasts were kept viable, in culture, for 68 days. Careful consideration of these findings and other prior art, led to the conclusion that, in a suitable novel system, providing continuous perfusion means and suitable loading means, viability might be maintained for a worthwhile period of study which could be up to 14 days or more.

The bone cores for our experiments were obtained from the trabecular bone of distal ulnae or femurs of 2 to 3 year old cows or femora or humeri of 2 to 3 year old pigs. Under sterile conditions throughout, the limb is first excised and then a 2.5 cm×2.5 cm×4.5 cm (proximo-distal dimension) sample of trabecular bone is cut from the central region of the proximal or distal metaphysis of the bone with a surgical hand saw and the proximal end is marked. The specimen is visually inspected under a dissecting microscope at 10× to assure that no growth plate scars are present.

Following isolation of the gross sample, 6×5 mm thick subspecimens are cut from it, under running sterile PBS at room temperature, using a band saw having a diamond tipped blade (Exact, Germany). Six bone core disks are then drilled in the proximo-distal direction, under sterile PBS, from each of the sub-specimens, using a 10 mm or 12 mm diamond tipped keyhole drill (Exact, Germany). The 6 bone cores from each 5 mm sub-specimen are randomized.

Each bone core disk is immediately marked on the proximal surface and placed in serum free medium for 20 minutes prior to placing it in the perfusion chamber apparatus of the present invention. Each sample is placed in the perfusion chamber such that it will be loaded from proximal to distal. The sample is then allowed 48 hours in the perfusion chamber in order to adapt, prior to any intervention. Thus, all experiments conducted using this protocol extend over 16 days, comprising 2 days for core adaptation and 14 days of intervention.

Using this method, bone disks may be cut with the necessary extreme precision to a flatness of ±0.2 microns and a parallelism of ±0.1 microns. The dimensions were selected in order to produce samples of a practical size for perfusion and in order to supply between 3,500,000–11,000,000 cells, based on an estimate of 10,000–20,000 cells per millimeter cube of bone (Mundy 1990; Parfitt 1983), which was considered sufficient to provide an adequate yield of markers for study.

Disk samples of trabecular bone, prepared according to the method immediately hereinbefore described, were perfused and maintained with circulating medium. The medium used was Ham's F10 containing 1%–5% FCS, 2 mg glutamine, streptomycin and penicillin G at 50,000 U/l, vitamin C 10 mg/ml, 0.12 g/l of $NaHCO_3$ and 10 mM Hepes. The medium was maintained at 37° C. and a pH of 7.1–7.3 for the total 14 days of the perfusion. The perfusion rate was 0.1 ml/minute and the medium was perfused using a 12 channel pump (Ismatec). The medium was changed at 12 hour intervals. The pH, $PCO_2$ and $PO_2$ were measured hourly for the first 5 hours then 12 hourly thereafter.

A series of FCS batches was tested for biological effect on the trabecular bone cores using alkaline phosphatase, cell viability and osteocalcin production. A sufficient quantity was retained from the most suitable batch of FCS to maintain a reproducible medium for the performance of the experimental program contemplated by the investigators. It is important to note that frozen FCS (−80° C.) has a maximum storage life of 3 years.

The flow rate through the explanted bone sample must be fast enough to maintain cell viability but not so fast that a shear force greater than 3 dynes/$cm^2$ is induced. When the flow rate is too slow, cells are inadequately oxygenated and lactate builds up. When the flow rate is too fast, the shear force, itself, causes increases in PGE2 and IGF-1. The flow rate of 0.1 ml/minute selected was determined as optimal by prior experiment with differing flow rates in order to provide sufficient effluent medium volume for sampling and analysis of PGE2, cAMP and IGF-1 and also in order to maintain $PO_2$ and $PCO_2$. $PO_2$ was monitored at each flow rate in these experiments to ensure adequate oxygenation of the cells in the bone explant perfusion/loading system.

Experiment 3—Injury Response Time (Establishment of Rest Period)

Cells placed in culture require time to adapt to their changed environment and this time period varied with the type of cell and the type of research we conducted. The necessary rest period for explanted trabecular bone samples in the instant system was determined. In our preliminary experiments, trabecular bone samples were perfused with culture medium plus 10% FCS. Under these conditions, IGF-1 increased from 5 to 14 hours and appeared to decline in the 15th hour, at the time the experiment was terminated.

Based on those preliminary data, a rest period of at least 48 hours was accepted as appropriate for IGF-1 to return to baseline level, before any intervention (mechanical loading, hormones, etc) was imposed on the bone explant organ culture. However, the adaptation time required was then documented over a series of full 24 hour periods to determine when the cells had recovered from the surgical trauma in order to determine the stable baseline condition from which intervention could be started.

Studies have provided the equivalent data for each of the second messengers, IGF-1 and certain other growth factors. Experiments to Investigate Cell Viability And Biomarkers under Varying Conditions Experiments were designed to investigate a variety of load magnitudes and frequencies, growth factors and applied active substances.

Specifically it was considered necessary to provide for the investigation of markers including the release of prostaglandin E2 (PGE2), cyclic-AMP (cAMP), inositol 1,4,5-trisphosphate (IP3) and insulin-like growth factor (IGF-1), in the perfusion effluent from explanted bone samples. These entities were to be studied during responses to stimuli including varying conditions of mechanical load and further, under the influence of biochemical stimulus with hormones, growth factors or drug substances.

The markers, produced by stimuli, immediately hereinbefore described, are important in the regulation of bone modeling and remodeling, at every age and nutritional level, in the adaptive response of the skeleton to such challenges.

Cell Viability a. Cell viability in samples of cow trabecular bone was determined at rest, at a maintenance load (the load at which the bone neither atrophies or hypertrophies) and at microstrains which ranged from 500 to 5000.

b. Oxygen utilization of the bone explant perfusion/loading model was determined at rest, at varied flow rates, at a maintenance load and at microstrains ranging from 500 to 5000.

Having established the flow rate limits for the instant perfusion chamber, experiments were conducted to verify cell viability. Percent viability at various time intervals was assessed in order to determine the number of cells still alive at any given time.

Two methods are commonly used to assess cell viability in cell culture. Alamar Blue Assay indicates succinate dehydrogenase activity in the cells. It incorporates an oxidation-reduction indicator that causes the Redox indicator to change from oxidized (non-fluorescent, blue) form to reduced (fluorescent, red) form in response to the cell metabolism in the culture medium. This assay is a general indicator of the metabolic function of the system but it does not allow quantification of cell viability, that is, calculating the percentage and distribution of viable cells. The use of MTT (sigma, 3-[4,5-Dimethylthiazol-2-yl]-2,5-diphenyltetrazolium bromide), does permit measurement of the number or percentage of live cells. In this assay, active mitochondrial dehydrogenases convert the water soluble MTT into an insoluble purple formazan by cleaving the tetrazolium ring. Cells with intact mitochondria will show a dark reddish/purple stain when tissue is viewed under a light microscope. Thus, mitochondrial staining is indicative of live cell function at the time MTT is administered. Since MTT is toxic to the cells, it can be used only at the end of an experiment. We used this method to determine the viability of cells after 14 days. At the end of perfusion runs, samples were perfused with MTT (30 mg/ml) for 6 hours then stabilized to 40° and sectioned to between 100 and 180 microns thick, using a diamond saw (EXACT, Germany), in order that viability throughout the sample could be investigated.

Somewhat less than 5% of the cells in the cow trabecular bone core, taken from the distal ulnae of 24 month old cows, died because of the surgical extraction and disk preparation procedure and of the remaining cells, more than 95% remained active throughout the 14 day studies.

Histological Assessment

Before loading the explanted bone samples, it was necessary to verify whole explant tissue viability over time.

MTT (30 mg/ml) was used as a cell viability marker. In one series of our cell viability experiments, four 14-day runs were conducted. In the first two runs, sample cores were processed with MTT every two days after a baseline core had been run for 8 hours and then removed. All cores were compared to the baseline core. 12 bone cores were perfused at a rate of 0.1 ml/minute. A baseline positive control viability sample was obtained 8 hours after the start of the experiment by perfusing a core with 30 mg/ml of MTT for 6 hours. The baseline sample and all other samples were perfused with serum free medium for the first 24 hours in order to collect 1 ml of medium for IGF-1 and PGE2 analysis. At the end of the 6 hour perfusion with MTT, the bone core was maintained at 4° C. at which time sections were cut using a diamond band saw. Sample sections were cut to a thickness between 100 and 180 microns in order that cell viability could be determined throughout the sample.

The base line sample (8 hours) was used as a positive control for viability. The number of viable cells in the 14 day sample showed no difference when compared to the positive control which had 95% viable cells. The sample sections taken from the top to the bottom of the sample demonstrated no difference in the number of cells showing the presence of MTT and the centers of all of the cores were found to be fully stained. However, there were a few trabecular areas that demonstrated cell death with no MTT present. It was felt that the diamond tipped keyhole drill used to excise the bone samples may have resulted in some damage in the outer few trabecular segments, resulting in tissue damage and cell death. It is clear from our results in this study that the bone cores obtained using this method and using the perfusion chamber apparatus of the present invention, can be maintained in a viable for 14 days.

Bioassay

Medium from the perfusion chamber to be used for the bioassay was sampled at varied time intervals according to the biomarker we chose to investigate. Pig osteoblasts obtained from Crenshaw (U of WI Madison) were characterized by alkaline phosphatase, collagen type 1 and the ability to produce bone nodules. Cells were plated out in 96-well, Nunclon, cell-culture grade, assay plates at a density of 45,000 cells per $cm^2$ in 100 ml per well of one of the following media:

Dulbecco's MEM

Dulbecco's BGJ (as used for the organ culture)

Ham's F-10

HI growth enhancement medium (Gibco)

The specific medium was chosen through trial and error depending on the best response of the markers we investigated (e.g. good for alkaline phosphatase and collagen). To the selected basic medium was added 10% FCS, ascorbic acid-2-phosphate at 5 mg/1 plus L-glutamine (or the stable analogue) for the first 24 hours. For the assay, the FCS is reduced from 10% to 1%, for 24 hours before the medium is replaced with medium from the perfusion culture. The control is unused medium used for the perfusion culture. Eight replicate wells were used for each sampling point. The cells were grown for 48 hours and then assayed for growth using the MTT method to measure succinate dehydrogenase activity. The MTT methods were calibrated against a known number of cells in a similar growth state; this was a control experiment using an agar plate and counting the cells with a cell counter. The presence of growth factors released from the perfusion culture were then assayed.

Loading

In loading experiments, the maximum compressive strain applied was 0.5% (5,000 $\mu E$) at 1 Hz sine wave. This equates to 20 cm compression at up to 50,000 $\mu E$ $sec^{-1}$.

The bone explant perfusion/loading system we have developed has allowed us to assess bone cellular response to specific stimuli under controlled conditions. An understanding of these mechanisms allows for their manipulation and in turn may lead to the possible alleviation or control of osteoporosis and other skeletal changes which result in the loss of skeletal integrity and function. The instant system provides investigators, for the first time, with effective means to study morphological changes in the skeletal tissue. In addition, the instant system permits the study of the physiological responses of the bone tissue under clearly defined and specified experimental conditions that can be set up to reflect the human activities of daily living and life style. The present invention also for the first time, permits the study of human bone biopsies in a controlled environment. This will not only enable investigators to identify morphologic changes that occur with different bone disease but will also permit the determination of the physiologic and possibly genetic determinants in such conditions.

It will be apparent to those skilled in the art that numerous modifications or changes may be made without departing from the spirit or the scope of either the present invention or its method of use. Thus the invention is only limited by the following claims.

We claim:

1. A mechanical testing device comprising:

a rigid frame;

a piezo translator connected to the frame, for translational movement of the piezo translator with respect to the frame;

a Wheatstone bridge connected to the piezo translator to produce an electrical signal related to the expansion of the piezo translator, wherein a sample positioned between the piezo translator and the frame is subjected to loads by the movement of the piezo translator;

a sensor which detects the force applied to the sample by the piezo translator, and produces a signal indicative of said force;

a computer which receives the Wheatstone bridge electrical signal and the signal indicative of the force applied to the sample, the computer controlling the advancement of the piezo translator to allow the application of precise amounts of compression to the sample.

2. The mechanical testing device of claim 1 wherein the piezo translator is controlled to allow the application of compression to the sample in increments at least as small as 200 nm.

3. A method for testing a sample comprising:

preparing a sample to have parallel top and bottom end surfaces;

placing the sample within a test apparatus having a frame, a piezo translator connected to the frame, for translational movement of the piezo translator with respect to the frame, the piezo translator having an output signal indicating the compression of the sample, and a force sensor between the sample and the frame;

applying a voltage to the piezo translator to advance the piezo translator to apply a desired level of compression:

detecting the output signal indicating level of compression of the sample, receiving and recording the outputs from the force sensor corresponding to the desired level of compression, and calculating material properties from said signal and said outputs.

* * * * *

UNITED STATES PATENT AND TRADEMARK OFFICE
CERTIFICATE OF CORRECTION

PATENT NO.    : 6,357,303 B2
DATED         : March 19, 2002
INVENTOR(S)   : Smith et al.

It is certified that error appears in the above-identified patent and that said Letters Patent is hereby corrected as shown below:

<u>Column 4,</u>
Line 50, replace "sec⁻" with -- $sec^{-1}$ --

<u>Column 19,</u>
Line 53, replace "20cm" with -- $20\mu m$ --

Signed and Sealed this

Twenty-fourth Day of September, 2002

Attest:

Attesting Officer

JAMES E. ROGAN
*Director of the United States Patent and Trademark Office*